(12) United States Patent
Zarif et al.

(10) Patent No.: US 6,592,894 B1
(45) Date of Patent: *Jul. 15, 2003

(54) HYDROGEL-ISOLATED COCHLEATE FORMULATIONS, PROCESS OF PREPARATION AND THEIR USE FOR THE DELIVERY OF BIOLOGICALLY RELEVANT MOLECULES

(75) Inventors: Leila Zarif, Branchburg, NJ (US); Tuo Jin, Highland Park, NJ (US); Ignacio Segarra, South Orange, NJ (US); Raphael J. Mannino, Annadale, NJ (US)

(73) Assignees: BioDelivery Sciences International, Inc., Newark, NJ (US); University of Medicine and Dentistry of New Jersey, Newark, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/613,840

(22) Filed: Jul. 11, 2000

Related U.S. Application Data

(63) Continuation-in-part of application No. 09/235,400, filed on Jan. 22, 1999, now Pat. No. 6,153,217.

(51) Int. Cl.⁷ ............................ A61K 9/127; A61K 9/00
(52) U.S. Cl. ..................... 424/450; 424/400; 424/417; 424/427; 424/430; 424/432; 424/434; 424/435; 424/436; 428/402.2; 261/4.1; 261/4.3

(58) Field of Search .................... 424/450, 1.21, 424/9.32, 9.51, 417, 94.3, 427, 430, 434, 435, 436; 428/402.2; 264/4.1, 4.3; 514/966, 967

(56) References Cited

U.S. PATENT DOCUMENTS 4,663,161 A * 5/1987 Mannino
5,994,318 A 11/1999 Gould-Fogerite et al.

FOREIGN PATENT DOCUMENTS

| WO | 96/25942 | * | 8/1996 |
| WO | 97 30725 A | | 8/1997 |
| WO | WO 9730725 A1 | | 8/1997 |
| WO | 97/30725 | * | 8/1997 |
| WO | 00 42989 A | | 7/2000 |
| WO | WO 0042989 A2 | | 7/2000 |

* cited by examiner

Primary Examiner—Gollamudi S. Kishore
(74) Attorney, Agent, or Firm—Lahive & Cockfield, LLP; Elizabeth A. Hanley

(57) ABSTRACT

A process for producing a small-sized, lipid-based cochleate. Cochleates are derived from liposomes which are suspended in an aqueous two-phase polymer solution, enabling the differential partitioning of polar molecule based-structures by phase separation. The liposome-containing two-phase polymer solution, treated with positively charged molecules such as $Ca_{2+}$ or $Zn_{2+}$, forms a cochleate precipitate of a particle size less than one micron. The process may be used to produce cochleates containing biologically relevant molecules.

38 Claims, 12 Drawing Sheets

US 6,592,894 B1

HYDROGEL-ISOLATED COCHLEATE FORMULATIONS, PROCESS OF PREPARATION AND THEIR USE FOR THE DELIVERY OF BIOLOGICALLY RELEVANT MOLECULES

CROSS-REFERENCE TO RELATED APPLICATION

This is a Continuation-in-Part of U.S. application No. 09/235,400 filed Jan. 22, 1999 now U.S. Pat. No. 6,153,217,

FIELD OF THE INVENTION

The present invention relates to a novel method for preparing a novel ipid-based cochleate delivery system, the preparations derived from the lipid-based cochleate delivery system, such as drugs, carbohydrates, vitamins, minerals, polynucleotides, polypeptides, lipids and the like, and the use of these preparations.

BACKGROUND OF THE INVENTION

The ability of biologically relevant molecules to be administered via the oral route depends on several factors. The biologically relevant molecule must be soluble in the gastrointestinal fluids in order for the biologically relevant molecule to be transported across biological membranes for an active transport mechanism, or have suitable small particle size that can be absorbed through the Peyer's Patches in the small intestine and through the lymphatic system. Particle size is an important parameter when oral delivery is to be achieved (see Couvreur et al, *Adv. Drug Delivery Rev.,* 10:141–162 (1993)).

The primary issue in the ability to deliver drugs orally is the protection of the drug from proteolytic enzymes. An ideal approach is to incorporate the drug in a hydrophobic material so that the aqueous fluids cannot penetrate the system. Lipid-based cochleates are an ideal system that can achieve this purpose.

The advantages of cochleates are numerous. The cochleates have a nonaqueous structure and therefore they:

a) are more stable because of less oxidation of lipids;

b) can be stored lyophilized, which provides the potential to be stored for long periods of time at room temperatures, making them advantageous for world-wide shipping and storage prior to administration;

c) maintain their structure even after lyophilization, whereas liposome structures are destroyed by lyophilization;

d) exhibit efficient incorporation of biologically relevant molecules into the lipid bilayer of the cochleate structure;

e) have the potential for slow release of a biologically relevant molecule in vivo as cochleates dissociate;

f) have a lipid bilayer which serves as a carrier and is composed of simple lipids which are found in animal and plant cell membranes, so that the lipids are non-toxic;

g) are produced easily and safely;

h) can be produced as defined formulations composed of predetermined amounts and ratios of drugs or antigens.

Cochleate structures have been prepared first by D. Papahadjopoulos as an intermediate in the preparation of large unilamellar vesicles (see U.S. Pat. No. 4,078,052). The use of cochleates to deliver protein or peptide molecules for vaccines has been disclosed in U.S. Pat. Nos. 5,840,707 and 5,643,574. The use of cochleates to orally deliver drugs, nutrients, and flavors have been described in U.S. Pat. No. 5,994,318.

However, the advantages of using small-sized cochleates have only recently been explored. The effective oral delivery of drugs that are mediated by hydrogel-isolated cochleates has been described in U.S. application Ser. No. 09/235,400. However, the effective delivery of hydrogel-isolated cochleates have not been described for other biologically relevant molecules such as drugs, polypeptides, polynucleotides, antigens, vitamins, minerals, amino acids, saccharides, flavor oils, and the like.

SUMMARY OF THE INVENTION

Accordingly, it is an object of this invention to provide a method for obtaining a hydrogel-isolated cochleate of a particle size of less than one micron. The method further comprises the steps required to encochleate at least one biologically relevant molecule in the hydrogel-isolated cochleates in an effective amount.

A "biologically relevant molecule" is one that has a role in the life processes of a living organism. The molecule may be organic or inorganic, a monomer or a polymer, endogenous to a host organism or not, naturally occurring or synthesized in vitro, and the like. Thus, examples include vitamins, minerals, flavors, amino acids, toxins, microbicides, microbistats, co-factors, enzymes, polypeptides, polypeptide aggregates, polynucleotides, lipids, carbohydrates, nucleotides, starches, pigments, fatty acids, hormones, cytokines, viruses, organelles, steroids and other multi-ring structures, saccharides, metals, metabolic poisons, drugs, and the like.

These and other objects have been obtained by providing an encochleated biologically relevant molecule, wherein the biologically relevant molecule-cochleate comprises the following components:

a) a biologically relevant molecule, b) a negatively charged lipid, and c) a cation component, wherein the article size of the cochleate is less than one micron.

BRIEF DESCRIPTION OF THE FIGS.

The large open circles are formed by the fusion of small dextran particles. Partition of liposomes favors the dextran phase as indicated by a yellow color of AmB. FIG. 3B: Microscopic images of the sample shown in FIG. 3A after treatment with $CaCl_2$ solution. The black objects in circles, are cochleates formed by the addition of $Ca^{2+}$ ions.

Figure 3A:
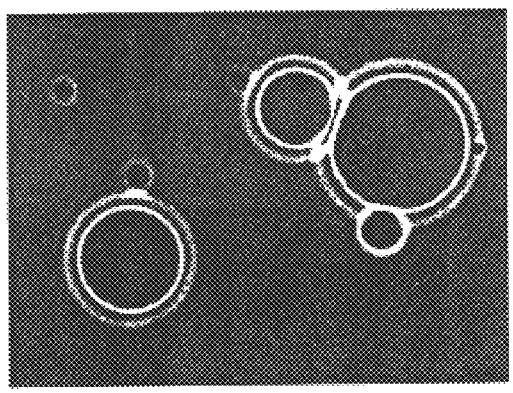
FIGS. 3A and 3B illustrate microscopic images of a mixture of liposomes in dextran dispersed into PEG gel solution. The small black dots are dextran particles formed by dispersing the dextran phase in the PEG phase.
Figure 3B:
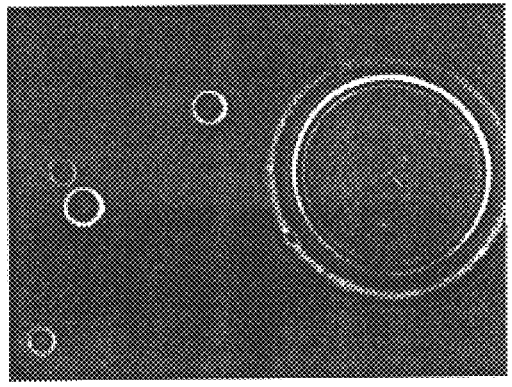
Figure 4A:
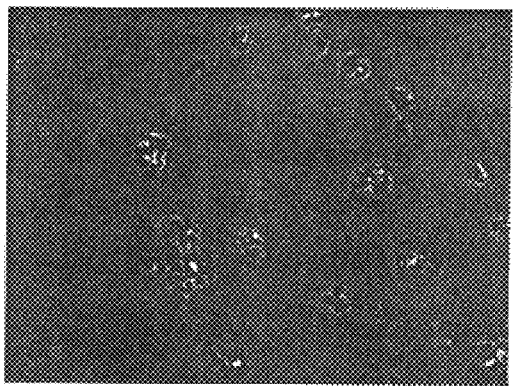
Figure 4B:
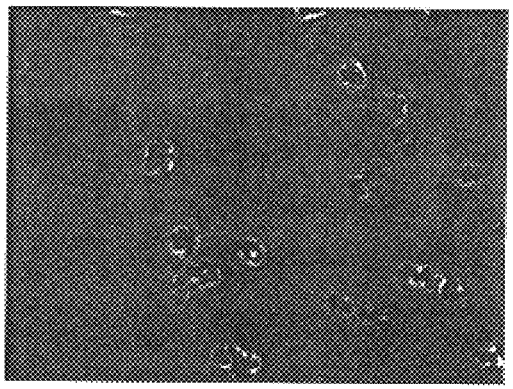
Figure 4C:
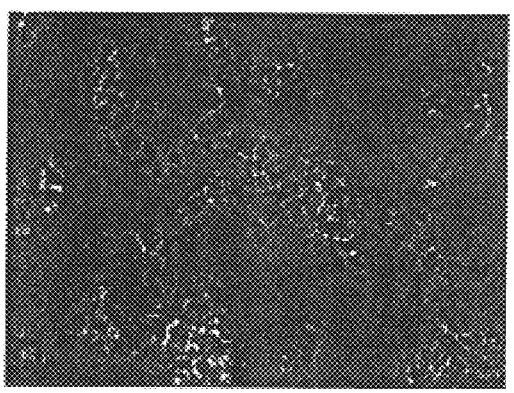
Figure 4D:
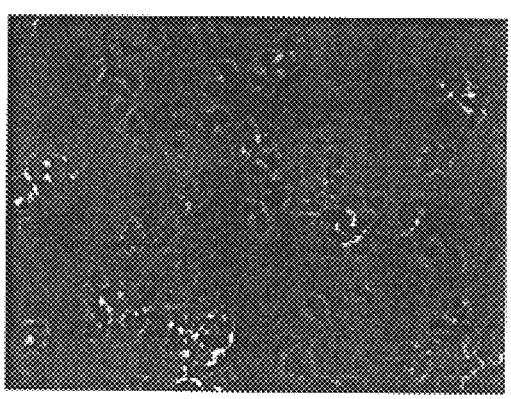
Figure 4E:
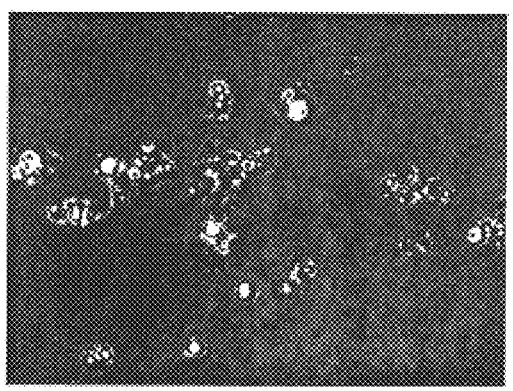
Figure 4F:
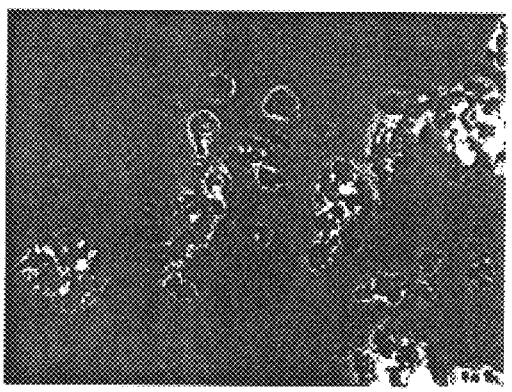

FIGS. 4A–4F illustrate microscopic images of the sample shown in FIGS. 3A and 3B after washing with a buffer containing 1 mM $CaCl_2$ and 100 mM NaCl. Aggregates are formed by the cochleate particles (FIG. 4B). A suspension shown in FIG. 4A following the addition of EDTA. Cochleate particles opened to liposomes with a diameter of 1–2 microns, indicating the intrinsic size of the cochleate particles is in the sub-micron range (FIG. 4C). AmB hydrogel-isolated cochleates precipitated with zinc according to the procedure described in Example 14 (FIG. 4D). Cochleates displayed in FIG. 4C after treatment with EDTA (FIG. 4E). Empty hydrogel-isolated cochleates precipitated with zinc according to the procedure described in Example 13 (FIG. 4F). Cochleates displayed in FIG. 4F are after treatment with EDTA.

Figure 5:

FIG. 5 illustrates micrographs of hydrogel-isolated cochleates after freeze fracture.

Figure 6:
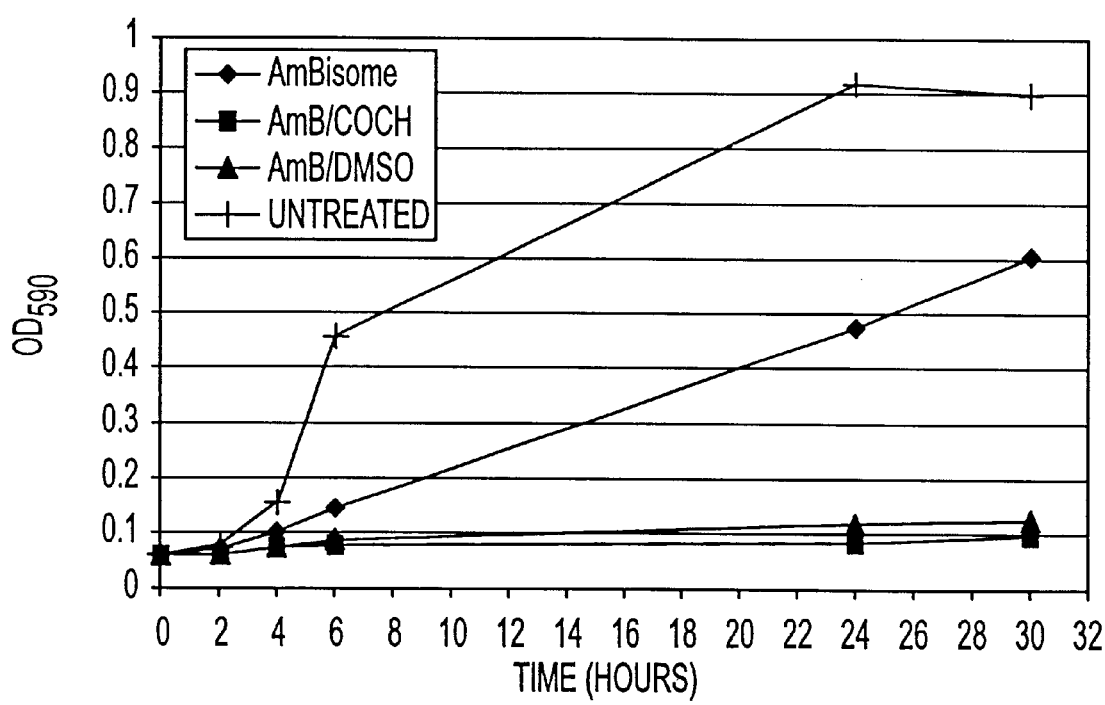

FIG. 6 illustrates growth inhibition of *Candida albicans* by hydrogel-isolated cochleates loaded with AmB at 0.625 μg AmB/ml. Comparison is made to AmB in DMSO and AmBisome$^R$.

Figure 7:
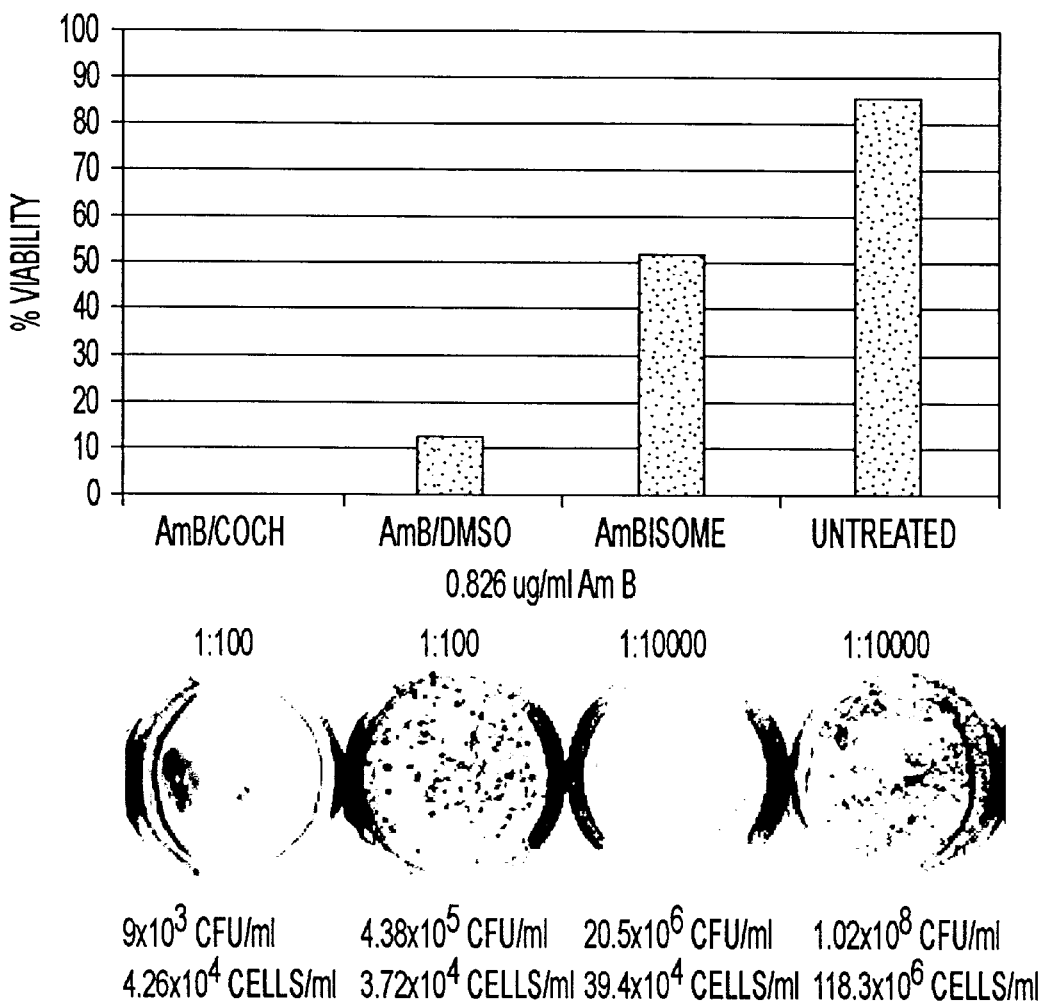

FIG. 7 illustrates the effect of hydrogel-isolated cochleates on the viability of *Candida albicans* after 30 hours.

Figure 8A:
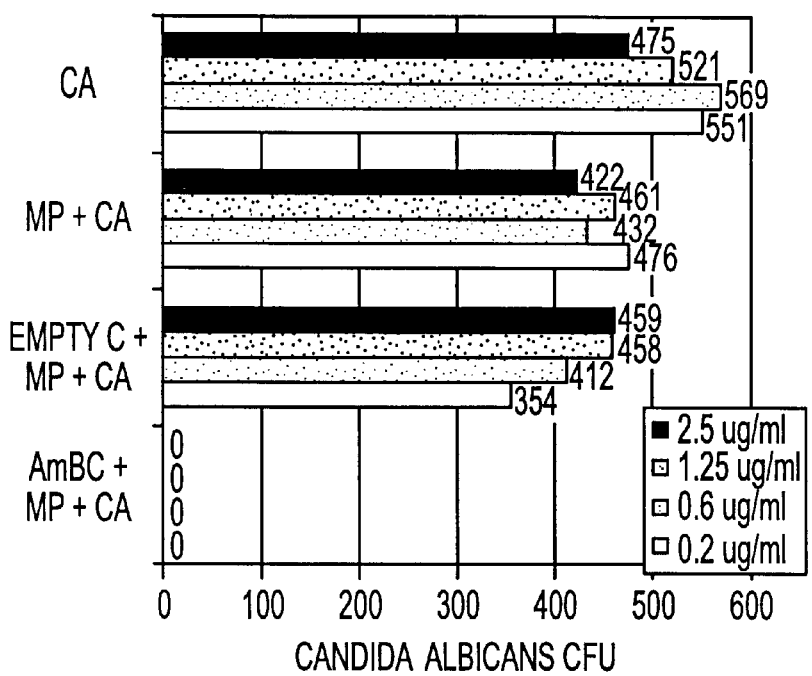
Figure 8B:
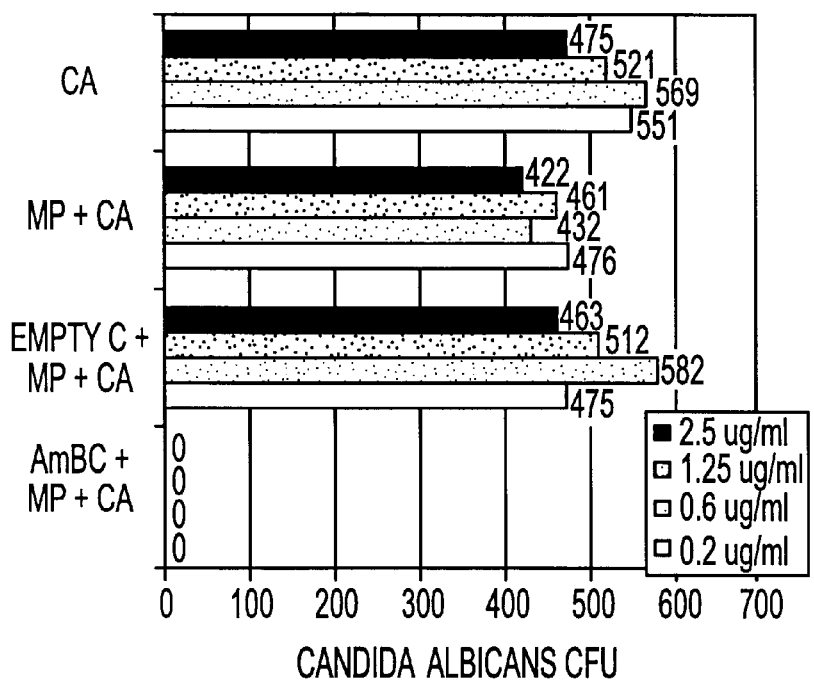

FIGS. 8A and 8B illustrate the efficacy of Amphotericin B-cochleates on macrophage cultures.

Figure 9:
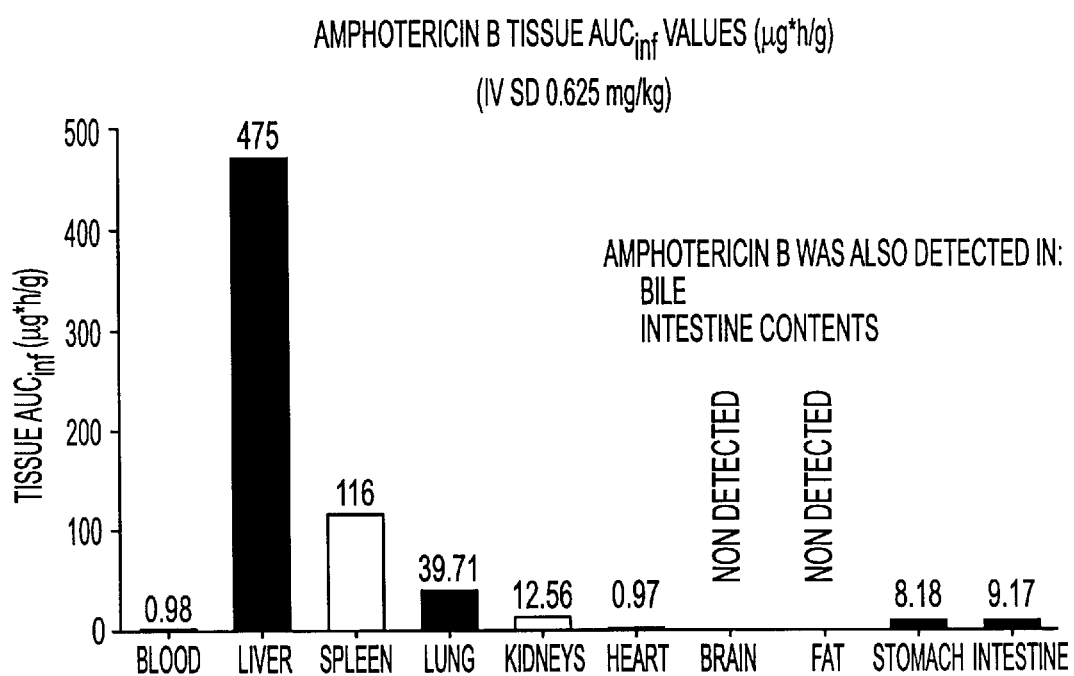

FIG. 9 illustrates Amphotericin B tissue levels after administration of Amphotericin B-cochleates.

Figure 10:
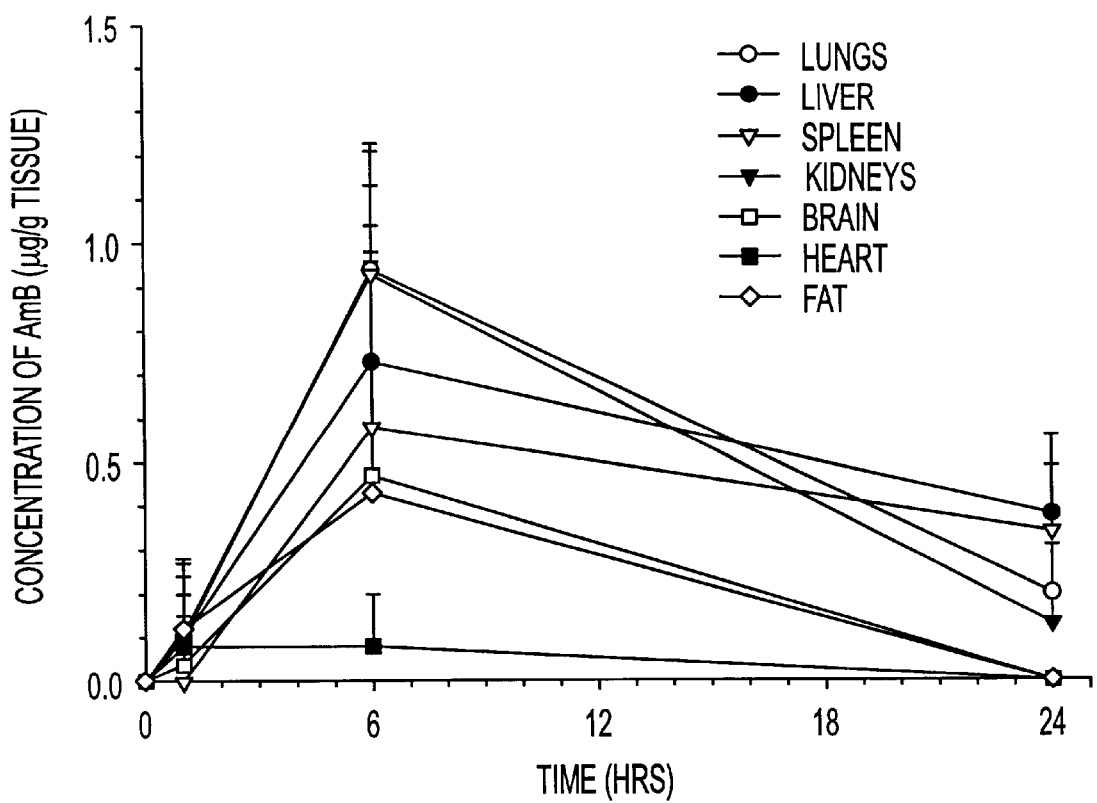

FIG. 10 illustrates the time profile tissue concentration of AmB after a single dose administration of hydrogel-isolated cochleates loaded with AmB.

Figure 11:
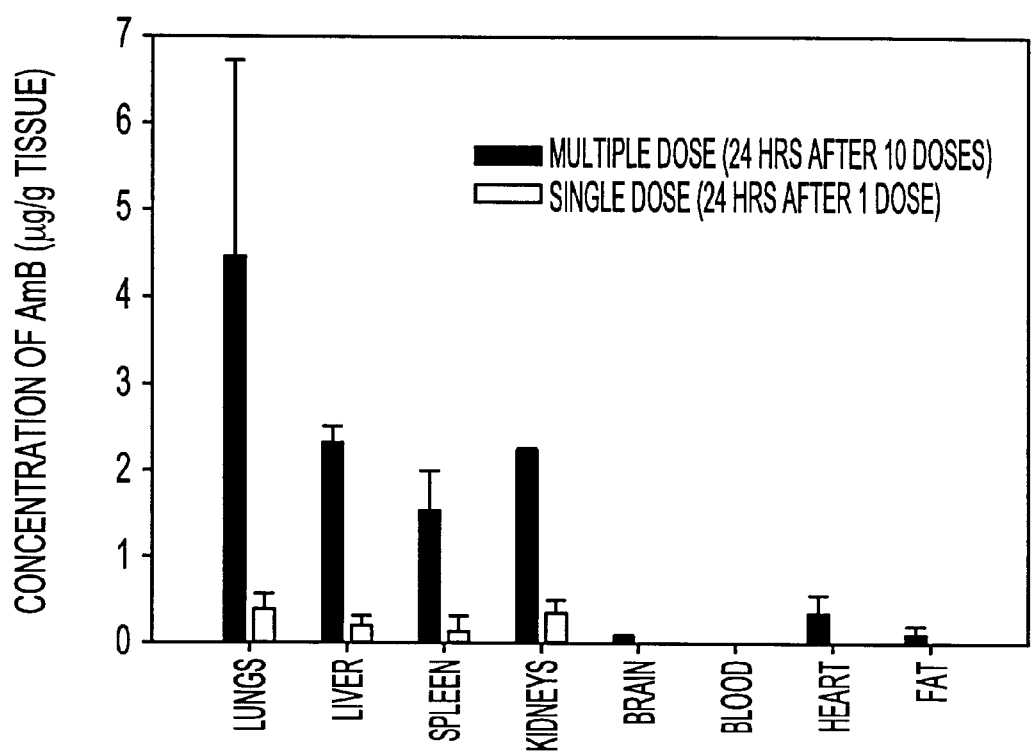

FIG. 11 illustrates AmB tissue level 24 hrs after single dose and 24 hrs after a multiple dose regime.

Figure 12:
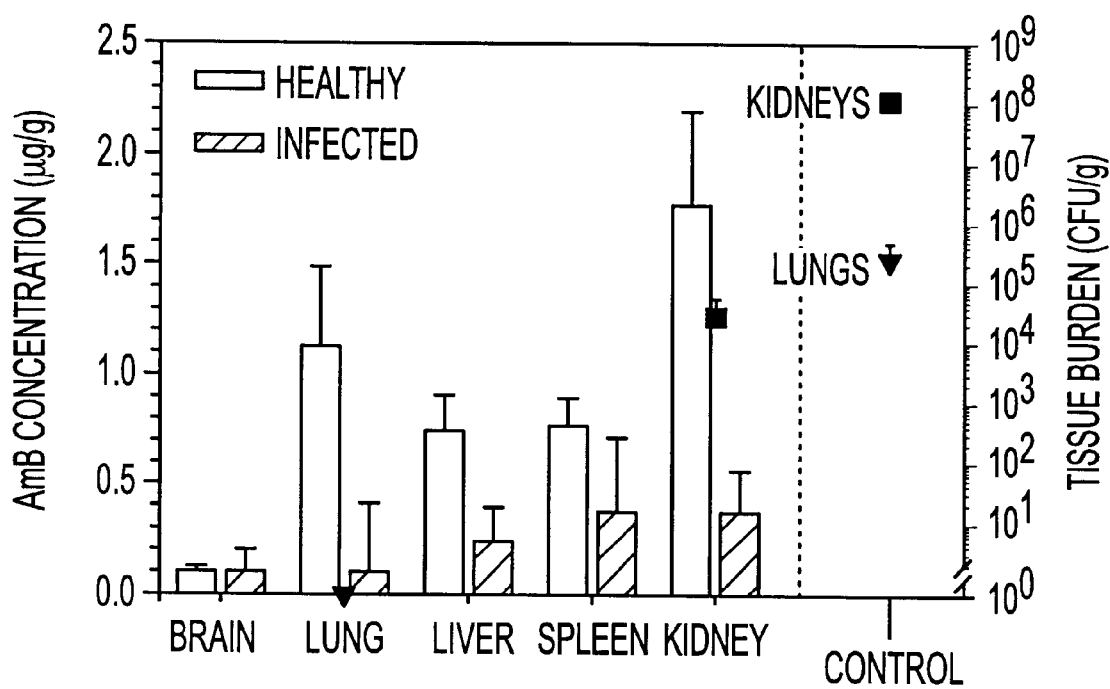

FIG. 12 illustrates correlation between Amphotericin B tissue level and the level of *Candida albicans* after administration of Amphotericin B cochleates.

DETAILED DESCRIPTION OF THE INVENTION

The present invention provides a solution to achieve effective oral delivery of drugs and other biologically relevant molecules by producing small-sized cochleates of less than one micron using new methods. The new approach is based on the incompatibility between two polymer solutions, both of which are aqueous. Aqueous two-phase systems of polymers are well used for protein purification due to a number of advantages such as freedom from the need for organic solvents, mild surface tension and the biocompatibility of aqueous polymers (see P. A. Albertsson, "Partition of cell particles and macromolecules", $_3$rd edition, Wiley N.Y. (1986); and "Separation using aqueous Phase System" D. Fisher Eds, Plenum N.Y. (1989)). It is known, for example, that large polar molecules such as proteins partition to a much higher concentration in a polymer phase with the physical characteristics similar to those of dextran than in a polymer phase with the physical characteristics similar to those of PEG (see Forciniti et al, *Biotechnol. Bioeng.*, 3:986 (1991)).

According to the present invention there are provided methods for preparing small-sized, lipid-based cochleate particles and preparations derived therefrom, comprising a biologically relevant molecule incorporated into the particles. The cochleate particles are formed of an alternating sequence of lipid bilayers/cation. The biologically relevant molecule is incorporated either in the lipid bilayers or in the interspace between the lipid bilayers. One of the methods for preparing the small-sized cochleates comprises: 1) preparing a suspension of small unilamellar liposomes or biologically relevant molecule-loaded liposomes, 2) mixing the liposome suspension with polymer A, 3) adding, preferably by injection, the liposome/Polymer A suspension into another polymer B in which polymer A is nonmiscible, leading to an aqueous two-phase system of polymers, 4) adding a solution of cation salt to the two-phase system of step 3, such that the cation diffuses into polymer B and then into the particles comprised of liposome/polymer A allowing the formation of small-sized cochleates, 5) washing the polymers out and resuspending the empty, drug or other biologically relevant molecule-loaded cochleates into a physiological buffer or any appropriate pharmaceutical vehicle.

A second method for preparing the small-sized cochleates comprises detergent and a biologically relevant molecule and cation. The detergent is added to disrupt the liposomes. The method comprises the following steps:

1) providing an aqueous suspension containing a detergent-lipid mixture;
2) mixing the detergent-lipid suspension with polymer A;
3) adding the detergent-lipid/polymer A suspension into a solution comprising polymer B, wherein polymer A and polymer B are immiscible, thereby creating a two-phase polymer system;
4) adding a solution of a cationic moiety to the two-phase polymer system; and
5) washing the two-phase polymer system to remove the polymer. A lyophilization procedure can be applied and the lyophilized biologically relevant molecule-cochleate complex can be filled into soft or hard gelatin capsules, tablets or other dosage form, for systemic, dermal or mucosal delivery.

Both methods described above lead to a small-sized particle with a narrow size range that allows efficient oral delivery of biologically relevant molecules. The biologically relevant molecule partitions into either or both lipid bilayers and interspace, and the biologically relevant molecule is released from the cochleate particles by dissociation of the particles in vivo. Alternative routes of administration may be systemic, such as intramuscular, subcutaneous or intravenous, or mucosal such as intranasal, intraocular, intravaginal, intraanal, or intrapulmonary. Appropriate dosages are determinable by, for example, dose-response experiments in laboratory animals or in clinical trials and taking into account body weight of the patient, absorption rate, half-life, disease severity and the like. The number of doses, daily dosage and course of treatment may vary from individual to individual. Other delivery routes can be dermal, transdermal or intradermal.

The first step of either method of the present invention, which is the preparation of small liposomes, can be achieved by standard methods such as sonication or microfluidization or other related methods (see, for example, Liposome Technology, Liposome Preparation and Related Techniques, Edited by Gregory Gregoriadis, Vol I, $2^{nd}$ Edition, CRC Press (1993)).

The second step of either method comprises the addition, preferably by injection, of polymer A/liposome suspension into polymer B can be achieved mechanically by using a syringe pump at an appropriate controlled rate, for example a rate of 0.1 ml/min to 50 ml/min, and preferably at a rate of 1 to 10 ml/min.

The formation of hydrogel-isolated cochleates (with or without a biologically relevant molecule) is achieved in the third step by adding a positively charged molecule to the aqueous two-phase polymer solution containing liposomes. The positively charged molecule can be a polyvalent cation and more specifically, any divalent cation that can induce the formation of a cochleate. In a preferred embodiment, the divalent cations include $Ca^{++}$, $Zn^{++}$, $Ba^{++}$ and $Mg^{++}$ or other elements capable of forming divalent ions or other structures having multiple positive charges capable of chelating and bridging negatively charged lipids, such as polycationic lipids. Addition of positively charged molecules to liposome-containing solutions is also used to precipitate cochleates from the aqueous solution.

To isolate the cochleate structures and to remove the polymer solution, cochleate precipitates are repeatedly washed in a fourth step with a buffer containing a positively charged molecule, and more preferably, a divalent cation. Addition of a positively charged molecule to the wash buffer ensures that the cochleate structures are maintained throughout the wash step, and that they remain as precipitates.

Finally, the medium in which the cochleates are suspended can contain salt such as calcium chloride, zinc chloride, cobalt chloride, sodium chloride, sodium sulfate, potassium sulfate, ammonium sulfate, magnesium sulfate and sodium carbonate. The medium can contain polymers, such as pluronics, and polyethylene glycols. The biologically relevant molecule-cochleate is made by diluting into an appropriate biologically acceptable carrier (e.g., a divalent cation-containing buffer).

The lipids of the present invention are non-toxic lipids and include, but are not limited to simple lipids which are found in animal and plant cell membranes. Preferably the lipid is a negatively charged lipid, more preferably a negatively charged phospholipid, and even more preferably a lipid from the group of phosphatidylserine, phosphatidylinositol, phosphatidic acid, and phosphatidyl glycerol. The lipids may also include minor amounts of zwitterionic lipids, cationic lipids, polycationic lipids or neutral lipids capable of forming hydrogen bonds to a biologically relevant molecule such as PEGylated lipid.

The polymers A and B of the present invention can be of any biocompatible polymer classes that can produce an aqueous two-phase system. For example, polymer A can be, but is not limited to, dextran 200,000–500,000, Polyethylene glycol (PEG) 3,400–8,000; polymer B can be, but is not limited to, polyvinylpyrrolidone (PVP), polyvinylalcohol (PVA), Ficoll 30,000–50,000, polyvinyl methyl ether (PVMB) 60,000–160,000, PEG 3,400–8,000. The concentration of polymer A can range from between 2–20% w/w as the final concentration depending on the nature of the polymer. The same concentration range can be applied for polymer B. Examples of suitable two-phase systems are Dextran/PEG, 5–20% w/w Dextran 200,000–500,000 in 4–10% w/w PEG 3,400–8,000; Dextran/PVP 10–20% w/w Dextran 200,000–500,000 in 10–20% w/w PVP 10,000–20,000; Dextran/PVA 3–15% w/w Dextran 200,000–500,000 in 3–15% w/w PVA 10,000–60,000; Dextran/Ficoll 10–20% w/w Dextran 200,000–500,000 in 10–20% w/w Ficoll 30,000–50,000; PEG/PVME 2–10% w/w PEG 3,500–35,000 in 6–15% w/w PVME 60,000–160,000.

The biologically relevant molecule is a molecule that has a role in the life processes of a living organism. The molecule may be organic or inorganic, a monomer or a polymer, charged, either positively or negatively, hydrophilic, amphiphilic or hydrophobic in aqueous media, endogenous to a host organism or not, naturally occurring or synthesized in vitro and the like.

The biologically relevant molecule may be a drug, and the drug may be an antiviral, an anesthetic, an anti-infectious, an antifungal, an anticancer, an immunosuppressant, a steroidal anti-inflammatory, a non-steroidal antiinflammatory, a tranquilizer or a vasodilatory agent. Examples include Amphotericin B, acyclovir, adriamycin, carbamazepine, melphalan, nifedipine, indomethacin, naproxen, estrogens, testosterones, steroids, phenytoin, ergotamines, cannabinoids, rapamycin, propanidid, propofol, alphadione, echinomycine, miconazole nitrate, teniposide, taxol, taxotere, nystatin, rifampin, and vitamin A acid.

The biologically relevant molecule may be a polypeptide such as cyclosporin, angiotensin I, II and III, enkephalins and their analogs, ACTH, anti inflammatory peptides I, II, III, bradykinin, calcitonin, beta-endorphin, dinorphin, leucokinin, leutinizing hormone releasing hormone (LHRH), insulin, neurokinins, somatostatin, substance P, thyroid releasing hormone (TRH) and vasopressin.

The biologically relevant molecule may be an antigen, but the antigen is not limited to a protein antigen. The antigen can also be a carbohydrate or a polynucleotide. Examples of antigenic proteins include envelope glycoproteins from viruses, animal cell membrane proteins, plant cell membrane proteins, bacterial membrane proteins and parasitic membrane proteins. Examples of a polynucleotide include a DNA or an RNA molecule. The polynucleotide can also be in the form of a plasmid DNA. The polynucleotide can be one that expresses a biologically active polypeptide, for example, an enzyme or a structural or housekeeping protein. Further, the polynucleotide need not be expressed, but may be an immunogen, a ribozyme or an antisense molecule.

The biologically relevant molecule may also be a nutrient such as vitamins, minerals, fatty acids, amino acids, and saccharides. Specific examples include vitamins A, D, E, or K; minerals such as calcium, magnesium, barium, iron or zinc; polyunsaturated fatty acids or essential oils; amino acids; and saccharides such as glucose and sucrose.

The biologically relevant molecule may also be a flavor substance. Examples include flavor substances generally associated with essential oils, such as cinnamon oil, and extracts obtained from botanical sources such as herbs, citrus, spices and seeds. Oils/extracts are sensitive to degradation by oxidation, and because the processing of the natural oils and extracts often involves multi-step operations, costs are generally considered to be higher. The advantage of an oil/extract-cochleate would be in the stabilization of these otherwise volatile and expensive flavor substances. Flavor-cochleates can also be incorporated into consumable food preparations as flavor enhancers.

The biologically relevant molecule is extracted from the source particle, cell, tissue, or organism by known methods. Biological activity of biologically relevant molecules need not be maintained. However, in some instances (e.g., where a protein has membrane fusion or ligand binding activity or a complex conformation which is recognized by the immune system), it is desirable to maintain the biological activity. In these instances, an extraction buffer containing a detergent which does not destroy the biological activity of the membrane protein is used. Suitable detergents include ionic detergents such as cholate salts, deoxycholate salts and the like or heterogeneous polyoxyethylene detergents, such as Tween, BRIG or Triton.

Utilization of this method allows reconstitution of antigens, more specifically proteins, into the liposomes with retention of biological activities, and eventually efficient association with the cochleates. This avoids organic solvents, sonication, or extreme pH, temperature, or pressure all of which may have an adverse effect upon efficient reconstitution of the antigen in a biologically active form.

Hydrogel-isolated cochleates may contain a combination of various biologically relevant molecules as appropriate.

The cochleate particles can be enteric. The cochleate particles can be placed within gelatin capsules and the capsule can be enteric coated.

In the preparations of the present invention certain hydrophobic materials can be added to provide enhanced absorption properties for oral delivery of biologically relevant molecules. These materials are preferably selected from the group consisting of long chain carboxylic acids, long chain carboxylic acid esters, long chain carboxylic acid alcohols and mixtures thereof. The hydrophobic materials can be added either initially to the lipid prior to the formation of liposomes or in a later step in the form of a fat vehicle such as an emulsion.

The skilled artisan can determine the most efficacious and therapeutic means for effecting treatment practicing the instant invention. Reference can also be made to any of numerous authorities and references including, for example, "Goodman & Gillman's, The Pharmaceutical Basis for Therapeutics", (6$^{th}$ Ed., Goodman et al., eds., MacMillan Publ. Co., New York (1980)).

The invention will now be described by examples which are not to be considered as limiting the invention. In the examples, unless otherwise indicated, all ratios, percents and amounts are by weight.

EXAMPLES

Example 1

Preparation of Empty Hydrogel-Isolated Cochleates from Dioleoylphosphatidylserine Precipitated with Calcium Step 1: Preparation of Small Unilamellar Vesicles from Dioleoylphosphatidylserine A solution of dioleoyl phosphatidylserine (DOPS, Avanti Polar Lipids, Alabaster, Ala., USA) in chloroform (10 mg/ml) was placed in a round-bottom flask and dried to a film using a Buchi rotavapor at 35° C. The rotavapor was sterilized by flashing nitrogen gas through a 0.2 µm filter. The following steps were carried out in a sterile hood. The dried lipid film was hydrated with de-ionized water at the concentration of 10 mg lipid/ml. The hydrated suspension was purged and sealed with nitrogen, then sonicated in a cooled bath sonicator (Laboratory Supplies Corn., Inc.). Sonication was continued (for several seconds to several minutes depending on lipid quantity and nature) until the suspension became clear (suspension A) and there were no liposomes apparently visible under a phase contrast microscope with a 1000× magnification. Laser light scattering (weight analysis, Coulter N4 Plus) indicated that the mean diameter was 35.7±49.7 nm.

Step 2: Preparation of Hydrogel-Isolated Cochleates

The liposome suspension obtained in step 1 was mixed with 40% w/w dextran-500,000 (Sigma) in a suspension of 2/1 v/v Dextran/liposome. This mixture was injected with a syringe into 15% w/w PEG-8,000 (Sigma) (PEG 8000/(suspension A)) under magnetic stirring to result in suspension B. The rate of the stirring was 800–1,000 rpm. A CaCl$_2$ solution (100 mM) was added to the suspension to reach the final concentration of 1 mM.

Figure 1:
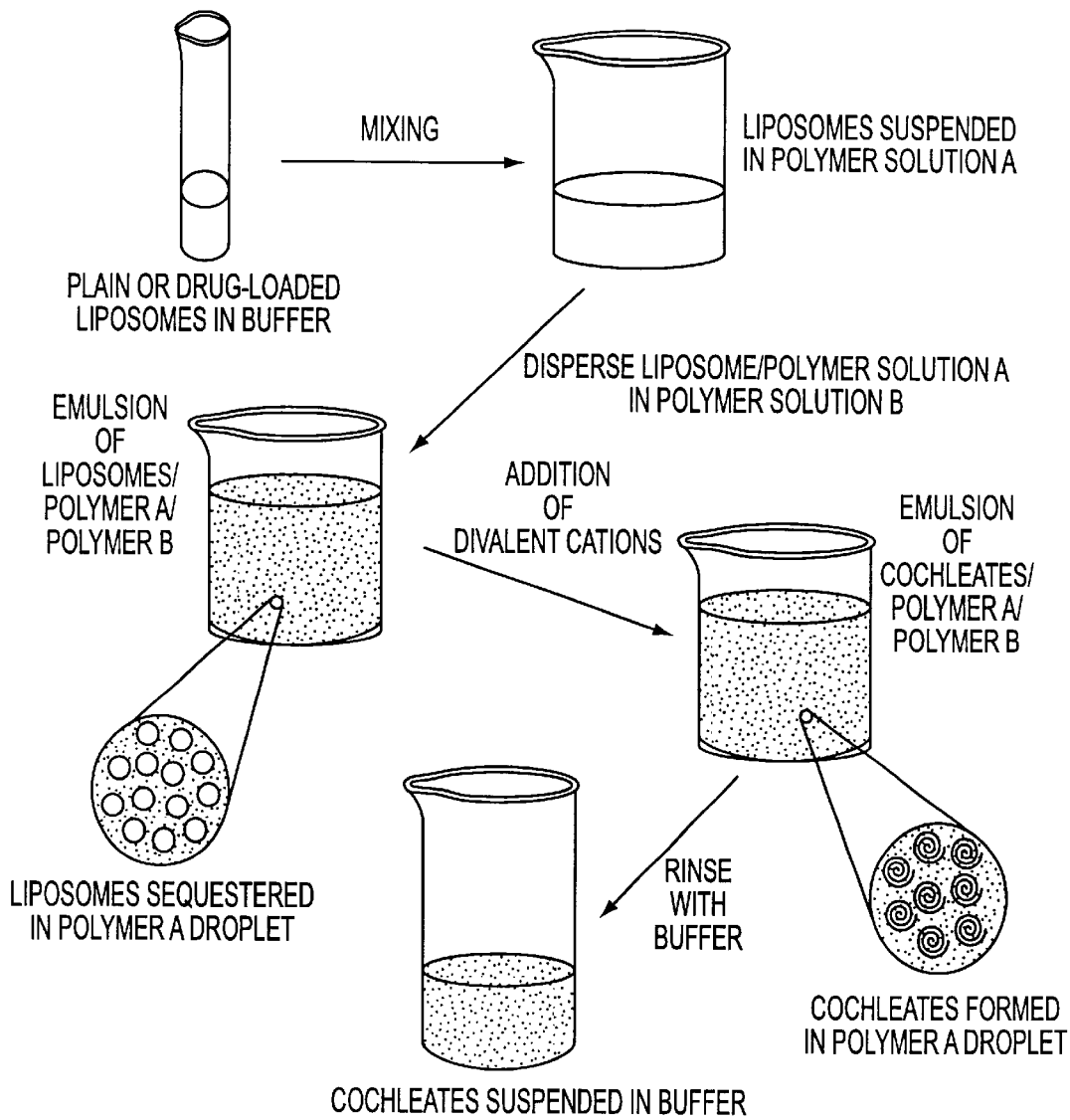
FIG. 1 is a schematic of the process by which the hydrogel-isolated cochleates of the present invention, with or without a biologically relevant molecule, are obtained.
Figure 2A:
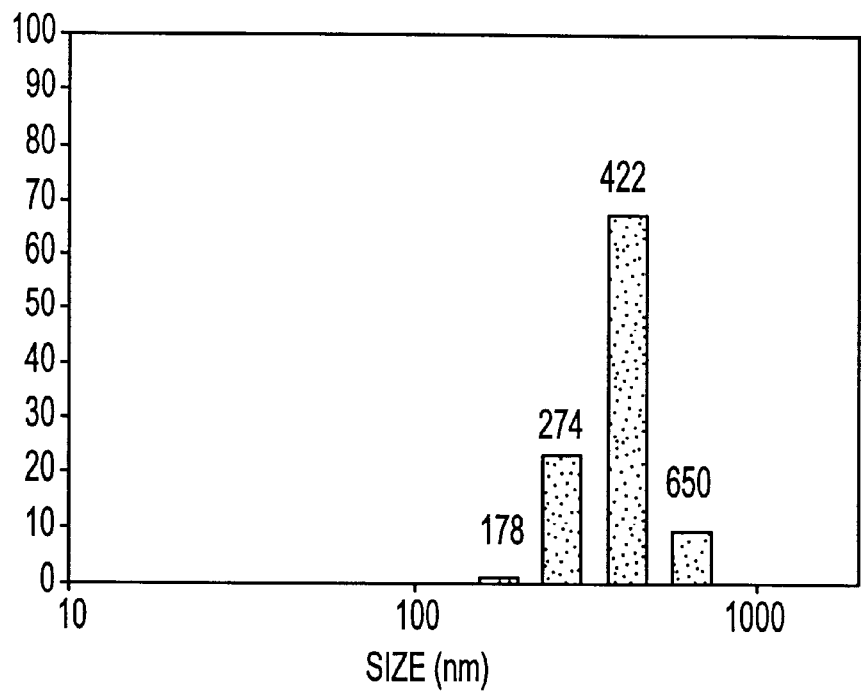
FIGS. 2A and 2B illustrate a particle size distribution (weight analysis) of hydrogel-isolated cochleates either loaded with amphotericin B (AmB) (FIG. 2A) or empty (FIG. 2B) as measured by laser light scattering.
Figure 2B:
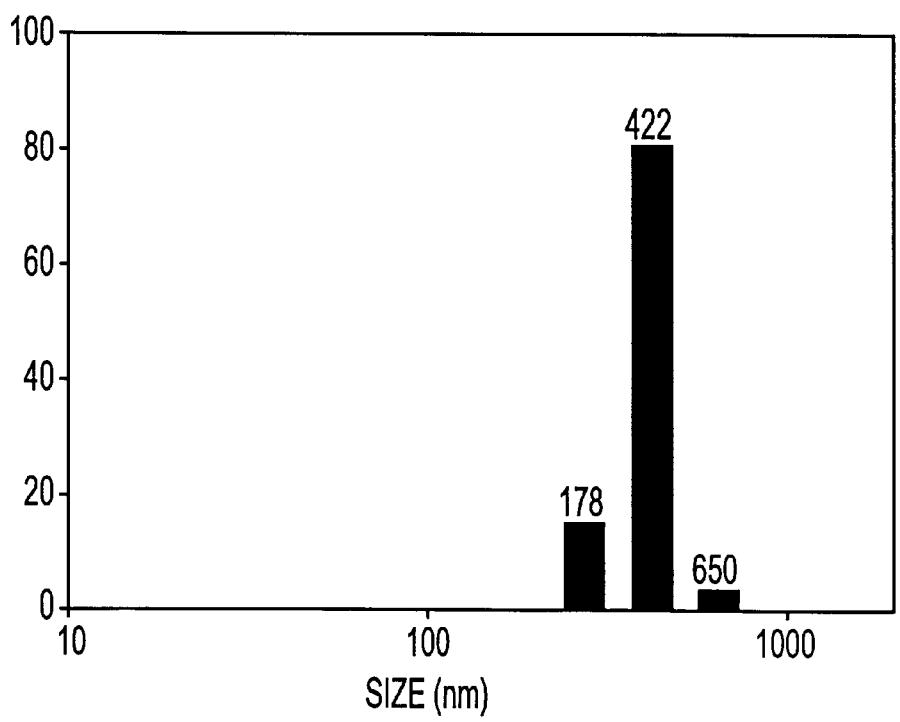

Stirring was continued for one hour, and then a washing buffer containing 1 mM CaCl$_2$ and 150 mM NaCl was added to suspension B at the volumetric ratio of 1:1. The suspension was vortexed and centrifuged at 3000 rpm, 2–4° C. for 30 min. After the supernatant was removed, additional washing buffer was added at the volumetric ratio of 0.5:1, followed by centrifugation under the same conditions. A schematic of this new method of obtaining cochleates is detailed in FIG. 1. The resultant pellet was reconstituted with the same buffer to the desired concentration. Laser light scattering (weight analysis, Coulter N4 Plus) indicates that the mean diameter for the cochleate is 407.2±85 nm (FIG. 2B).

Example 2

Preparation of Empty Hydrogel-Isolated Cochleates from a Mixture of Dioleoylphosphatidylserine and 1,2-Distearoyl-sn-glycerol-3-phosphoethanolamine-n-(poly(ethylene glycol)-5000, DSPE-PEG) Precipitated with Calcium Step 1: Preparation of Small Unilamellar Vesicles A solution of dioleoylphosphatidylserine (DOPS) and 1,2-distearoyl-sn-glycerol-3-phosphoethanolamine-n-(poly(ethylene glycol)-5000), (DSPE-PEG, Avanti Polar Lipids, Alabaster, Ala., USA) in chloroform (ratio of DOPS:DSPS-PEG=100:1, w:w) was placed in a round-bottom flask and dried to a film using a Buchi rotavapor at 35° C. The rotavapor was sterilized by flashing nitrogen gas through a 0.2 µm filter. The following steps were carried out in a sterile hood. The dried lipid film was hydrated with de-ionized water to a concentration of 10 mg lipid/ml. The hydrated suspension was purged and sealed with nitrogen, then sonicated in a cooled bath sonicator (Laboratory Supplies Corn., Inc.). Sonication was continued (for several seconds to several minutes depending on lipid quantity and nature) until the suspension became clear (suspension A) and there were no liposomes apparently visible under a phase contrast optical microscope with a 1000× magnification.

Step 2: Preparation of Hydrogel-Isolated Cochleates

The liposome suspension obtained in Step 1 was mixed with 40% w/w dextran-500,000 in a suspension of 2/1 v/v Dextran/liposome. This mixture was injected via a syringe into 15% w/w PEG-8,000 (PEG 8000/(suspension A)) under magnetic stirring to result in suspension B. The rate of the stirring was 800–1,000 rpm. A CaCl$_2$ solution (100 mM) was added to the suspension to reach the final concentration of 1 mM.

Stirring was continued for one hour, and then a washing buffer containing 1 mM CaCl$_2$ and 150 mM NaCl was added to suspension B at the volumetric ratio of 1:1. The suspension was vortexed and centrifuged at 3000 rpm, 2–4° C. for 30 min. After the supernatant was removed, additional washing buffer was added at the volumetric ratio of 0.5:1, followed by centrifugation under the same conditions. (See FIG. 1). The resulting pellet was reconstituted with the same buffer to the desired concentration. Phase contrast optical microscopy indicates the formation of uniform, very small, needle-like cochleates.

Example 3

Preparation of Empty Hydrogel-Isolated Cochleates from a Mixture of Dioleoylphosphatidylserine and n-octyl-beta-D-gluco-pyranoside Precipitated with Calcium Step 1: Preparation of Small Unilamellar Vesicles A solution of dioleoylphosphatidylserine (DOPS) in chloroform was placed in a round-bottom flask and dried to a film using a Buchi rotavapor at 35° C. The rotavapor was sterilized by flashing nitrogen gas through a 0.2 µm filter. The following steps were carried out in a sterile hood. The dried lipid film was hydrated with a solution of n-octyl-beta-D-gluco-pyranoside (OCG) at 1 mg/ml at a ratio of DOPS:OCG of 10:1 w:w. The hydrated suspension was purged and sealed with nitrogen, then sonicated briefly in a cooled bath sonicator.

Step 2: Preparation of Hydrogel-Isolated Cochleates

The suspension obtained in Step 1 was mixed with 40% w/w dextran-500,000 in a suspension of 2/1 v/v Dextran/liposome. This mixture was injected via a syringe into 15% w/w PEG-8,000 (PEG 8000/(suspension A)) under magnetic stirring to result in suspension B. The rate of the stirring was 800–1,000 rpm. A CaCl$_2$ solution (100 mM) was added to the suspension to reach the final concentration of 1 mM.

Stirring was continued for one hour, and then a washing buffer containing 1 mM CaCl$_2$ and 150 mM NaCl was added to suspension B at the volumetric ratio of 1:1. The suspension was vortexed and centrifuged at 3000 rpm, 2–4 C, for 30 min. After the supernatant was removed, additional washing buffer was added at the volumetric ratio of 0.5:1, followed by centrifugation under the same conditions (see FIG. 1). The resulting pellet was reconstituted with the same buffer to the desired concentration. Phase contrast optical microscopy indicates the formation of uniform, very small, needle-like cochleates.

Example 4

Preparation of Amphotericin B-loaded Hydrogel-Isolated Cochleates Precipitated with Calcium Step 1: Preparation of Small Unilamellar AmB-Loaded, Vesicles from Dioleoylphosphatidylserine A mixture of dioleoyl phosphatidylserine (DOPS) in chloroform (10 mg/ml) and AmB in methanol (0.5 mg/ml) at a molar ratio of 10:1 was placed in a round-bottom flask and dried to a film using a Buchi rotavapor at 40° C. The rotavapor was sterilized by flashing nitrogen gas through a 0.2 μm filter. The following steps were carried out in a sterile hood. The dried lipid film was hydrated with de-ionized water at the concentration of 10 mg lipid/ml. The hydrated suspension was purged and sealed with nitrogen, then sonicated in a cooled bath sonicator. Sonication was continued (for several seconds to several minutes depending on lipid quantity and nature) until the suspension became clear yellow (suspension A) and there were no liposomes apparently visible under a phase contrast microscope with a 1000× magnification.

Step 2: Preparation of AmB-loaded, Hydrogel-Isolated Cochleates.

The liposome suspension obtained in Step 1 was then mixed with 40% w/w dextran-500,000 in a suspension of 2/1 v/v Dextran/liposome. This mixture was then injected via a syringe into 15% w/w PEG-8,000 (PEG 8000/(suspension A)) under magnetic stirring to result in suspension B. The rate of the stirring was 800–1,000 rpm. A CaCl$_2$ solution (100 mM) was added to the suspension to reach the final concentration of 1 mM.

Stirring was continued for one hour, and then a washing buffer containing 1 mM CaCl$_2$ and 150 mM NaCl was added to suspension B at the volumetric ratio of 1:1. The suspension was vortexed and centrifuged at 3000 rpm, 2–4° C. for 30 min. After the supernatant was removed, additional washing buffer was added at the volumetric ratio of 0.5:1, followed by centrifugation under the same conditions (see FIG. 1). The resulting pellet was reconstituted with the same buffer to the desired concentration. Laser light scattering (weight analysis, Coulter N4 Plus) indicated that the AmB-cochleates mean diameter was 407.3±233.8 nm (FIG. 2A).

Example 5

Preparation of Doxorubicin (DXR)-Loaded Hydrogel-Isolated Cochleates Precipitated with Calcium Step 1: Preparation of Small Unilamellar DXR-Loaded Vesicles from Dioleoylphosphatidylserine A mixture of dioleoylphosphatidylserine (DOPS) in chloroform (10 mg/ml) and (DXR) in methanol (0.5 mg/ml) at a molar ratio of 10:1 was placed in a round-bottom flask and dried to a film using a Buchi rotavapor at room temperature. The rotavapor was sterilized by flashing nitrogen gas through a 0.2 μm filter. The following steps were carried out in a sterile hood. The dried lipid film was hydrated with de-ionized water at the concentration of 25 mg lipid/ml. The hydrated suspension was purged and sealed with nitrogen, then sonicated in a cooled bath sonicator. Sonication was continued (for several seconds to several minutes depending on lipid quantity and nature) until the suspension became clear pink (suspension A) and there were no liposomes apparently visible under phase contrast microscope with a 1000× magnification.

Step 2: Preparation of DXR-Loaded. Hydrogel-Isolated Cochleates

Five milliliters of the liposome suspension obtained in step 1 was mixed with 40% w/w dextran-500,000 (Sigma) in a suspension of 2/1 v/v Dextran/liposome. This mixture was injected via a syringe into 15% w/w PEG-8,000 (PEG 8000/(suspension A)) under magnetic stirring to result in suspension B. The rate of the stirring was 800–1,000 rpm. A CaCl$_2$ solution (100 mM) was added to the suspension to reach the final concentration of 1 mM.

Stirring was continued for one hour, and then a washing buffer containing 1 mM CaCl$_2$ and 150 mM NaCl was added to suspension B at the volumetric ratio of 1:1. The suspension was vortexed and centrifuged at 6400 rpm, 2–4° C. for 30 min (see FIG. 1). The resulting pellet was reconstituted with the same buffer to the desired concentration. Laser light scattering (weight analysis, Coulter N4 Plus) confirmed the formation of small DXR-cochleates.

Example 6

Preparation of Cyclosporin A (CSPA)-Loaded Hydrogel-Isolated Cochleates Precipitated with Calcium Step 1: Preparation of Small Unilamellar CSPA-Loaded Vesicles from Dioleoylphosphatidylserine A mixture of dioleoylphosphatidylserine (DOPS) in chloroform (10 mg/ml) and CSPA in methanol (0.5 mg/ml) at a molar ratio of 10:1 was placed in a round-bottom flask and dried to a film using a Buchi rotavapor at room temperature. The rotavapor was sterilized by flashing nitrogen gas through a 0.2 μm filter. The following steps were carried out in a sterile hood. The dried lipid film was hydrated with de-ionized water at the concentration of 10 mg lipid/ml. The hydrated suspension was purged and sealed with nitrogen, then sonicated in a cooled bath sonicator. Sonication was continued (for several seconds to several minutes depending on lipid quantity and nature) until the suspension became clear (suspension A) and there were no liposomes apparently visible under a phase contrast microscope with a 1000× magnification.

Step 2: Preparation of CSPA-Loaded, Hydrogel-Isolated Cochleates

The liposome suspension obtained in Step 1 was mixed with 40% w/w dextran-500,000 in a suspension of 2/1 v/v Dextran/liposome. This mixture was injected via a syringe into 15% w/w PEG-8,000 (Sigma) (PEG 8000/(suspension A)) under magnetic stirring to result in suspension B. The rate of the stirring was 800–1,000 rpm. A CaCl$_2$ solution (100 mM) was added to the suspension to reach the final concentration of 1 mM.

Stirring was continued for one hour, and then a washing buffer containing 1 mM CaCl$_2$ and 150 mM NaCl was added to suspension B at the volumetric ratio of 1:1. The suspension was vortexed and centrifuged at 3000 rpm, 2–4° C. for 30 min. After the supernatant was removed, additional washing buffer was added at the volumetric ratio of 0.5:1, followed by centrifugation under the same conditions (see FIG. 1). The resulting pellet was reconstituted with the same buffer to the desired concentration. Laser light scattering (weight analysis, Coulter N4 Plus) confirmed the formation of small CSPA-cochleates.

Example 7

Preparation of Nelfinavir (NVIR)-Loaded Hydrogel-Isolated Cochleates Precipitated With Calcium

Step 1: Preparation of Small Unilamellar NVIR-Loaded Vesicles from Dioleoylphosphatidylserine A mixture of dioleoylphosphatidylserine (DOPS) in chloroform (10 mg/ml) and NVIR in methanol (0.5 mg/ml) at a molar ratio of 10:1 was placed in a round-bottom flask and dried to a film using a Buchi rotavapor at RT. The rotavapor was sterilized by flashing nitrogen gas through a 0.2 $\mu$m filter. The following steps were carried out in a sterile hood. The dried lipid film was hydrated with de-ionized water at the concentration of 10 mg lipid/ml. The hydrated suspension was purged and sealed with nitrogen, then sonicated in a cooled bath sonicator. Sonication was continued (for several seconds to several minutes depending on lipid quantity and nature) until the suspension became clear (suspension A) and there were no liposomes apparently visible under a phase contrast microscope with a 1000× magnification.

Step 2: Preparation of NVIR-Loaded, Hydrogel-Isolated Cochleates

The liposome suspension obtained in Step 1 was mixed with 40% w/w dextran-500,000 in a suspension of 2/1 v/v Dextran/liposome. This mixture was injected via a syringe into 15% w/w PEG-8,000 (PEG 8000/(suspension A)) under magnetic stirring to result in suspension B. The rate of the stirring was 800–1,000 rpm. A $CaCl_2$ solution (100 mM) was added to the suspension to reach the final concentration of 1 mM.

Stirring was continued for one hour, and then a washing buffer containing 1 mM $CaCl_2$ and 150 mM NaCl was added to suspension B at the volumetric ratio of 1:1. The suspension was vortexed and centrifuged at 3000 rpm, 2–4° C. for 30 min. After the supernatant was removed, additional washing buffer was added at the volumetric ratio of 0.5:1, followed by centrifugation under the same conditions (see FIG. 1). The resulting pellet was reconstituted with the same buffer to the desired concentration. Laser light scattering (weight analysis, Coulter N4 Plus) confirmed the formation of small NVIR-cochleates.

Example 8

Preparation of Rifampin (RIF)-Loaded Hydrogel-Isolated Cochleates Precipitated with Calcium

Step 1: Preparation of Small Unilamellar RIF-Loaded Vesicles from Dioleoylphosphatidylserine A mixture of dioleoylphosphatidylserine (DOPS) in chloroform (10 mg/ml) and RIF in methanol (0.5 mg/ml) at a molar ratio of 10:1 was placed in a round-bottom flask and dried to a film using a Buchi rotavapor at RT. The rotavapor was sterilized by flashing nitrogen gas through a 0.2 $\mu$m filter. The following steps were carried out in a sterile hood. The dried lipid film was hydrated with de-ionized water at the concentration of 10 mg lipid/ml. The hydrated suspension was purged and sealed with nitrogen, then sonicated in a cooled bath sonicator. Sonication was continued (for several seconds to several minutes depending on lipid quantity and nature) until the suspension became clear (suspension A) and there were no liposomes apparently visible under a phase contrast microscope with a 1000× magnification.

Step 2: Preparation of RIF-Loaded, Hydrogel-Isolated Cochleates

The liposome suspension obtained in step 1 was mixed with 40% w/w dextran-500,000 (Sigma) in a suspension of 2/1 v/v Dextran/liposome. This mixture was injected via a syringe into 15% w/w PEG-8,000 (Sigma) (PEG 8000/ (suspension A)) under magnetic stirring to result in suspension B. The rate of the stirring was 800–1,000 rpm. A $CaCl_2$ solution (100 mM) was added to the suspension to reach the final concentration of 1 mM.

Stirring was continued for one hour, and then a washing buffer containing 1 mM $CaCl_2$ and 150 mM NaCl was added to suspension B at the volumetric ratio of 1:1. The suspension was vortexed and centrifuged at 3000 rpm, 2–4° C. for 30 min. After the supernatant was removed, additional washing buffer was added at the volumetric ratio of 0.5:1, followed by centrifugation under the same conditions (see FIG. 1). The resulting pellet was reconstituted with the same buffer to the desired concentration. Laser light scattering (weight analysis, Coulter N4 Plus) confirmed the formation of small RIF-cochleates.

Example 9

Preparation of Vitamin A acid-Loaded Hydrogel-Isolated Cochleates Precipitated with Calcium

Step 1: Preparation of Small Unilamellar Vitamin A-Loaded Vesicles from Dioleoylphosphatidylserine Vitamin A acid (retinoic acid) is sensitive to air oxidation and is inactivated by UV light. Vitamin A is protected when embedded into lipid bilayers. The incorporation is achieved as follows:

A mixture of dioleoylphosphatidylserine (DOPS) in chloroform (10 mg/ml) and Vitamin A in methanol (0.5 mg/ml) at a molar ratio of lipid/vitamin A of 10:1 was placed in a round-bottom flask and dried to a film using a Buchi rotavapor at RT. The rotavapor was sterilized by flashing nitrogen gas through a 0.2 $\mu$m filter. The following steps were carried out in a sterile hood. The dried lipid film was hydrated with de-ionized water at the concentration of 10 mg lipid/ml. The hydrated suspension was purged and sealed with nitrogen, then sonicated in a cooled bath sonicator. Sonication was continued (for several seconds to several minutes depending on lipid quantity and nature) until the suspension became clear (suspension A) and there were no liposomes apparently visible under a phase contrast microscope with a 1000× magnification.

Step 2: Preparation of Vitamin A-Loaded, Hydrogel-Isolated Cochleates

The liposome suspension obtained in Step 1 was mixed with 40% w/w dextran-500,000 in a suspension of 2/1 v/v Dextran/liposome. This mixture was injected via a syringe into 15% w/w PEG-8,000 in a ratio of suspension A/PEG of ½ V/V (PEG 8000/(suspension A)) under magnetic stirring to result in suspension B. The rate of the stirring was 800–1,000 rpm. A $CaCl_2$ solution (100 mM) was added to the suspension to reach the final concentration of 1 mM.

Stirring was continued for one hour, and then a washing buffer containing 1 mM $CaCl_2$ and 150 mM NaCl was added to suspension B at the volumetric ratio of 1:1. The suspension was vortexed and centrifuged at 3000 rpm, 2–4° C. for 30 min. After the supernatant was removed, additional washing buffer was added at the volumetric ratio of 0.5:1, followed by centrifugation under the same conditions (see FIG. 1). The resulting pellet was reconstituted with the same buffer to the desired concentration. The amount of vitamin A encapsulated in the cochleates was determined by UV absorption at 346 nm and it was found that more than 90% of the initial vitamin A was associated with the cochleates.

Example 10

Preparation of Polyunsaturated Fatty Acid (PFA)-Loaded Hydrogel-Isolated Cochleates Precipitated with Calcium PFA's are biologically relevant molecules involved in the control of the level of cholesterol in blood and are the precursors of prostaglandins. PFA's are sensitive to oxidation which limits their incorporation into food. PFA's undergo, in the presence of oxygen, a series of reactions called autoxidation, leading to aldehydes and then ketones which have a fishy unpleasant odor and flavor. Embedding PFA in rigid, rolled-up, lipid bilayers helps prevent the autoxidation cascade. A general method of preparing PFA-cochleates is as follows:

Step 1: Preparation of Small Unilamellar PFA-Loaded Vesicles from Dioleoylphosphatidylserine A mixture of dioleoylphosphatidylserine in chloroform (10 mg/ml) and PFA in methanol (0.5 mg/ml) at a molar ratio of 10:1 was placed in a round-bottom flask and dried to a film using a rotary evaporator at RT. The rotary evaporator was sterilized by flashing nitrogen gas through a 0.2 µm filter. The following steps were carried out in a sterile hood. The dried lipid film was hydrated with de-ionized water at the concentration of 10 mg lipid/ml. The hydrated suspension was purged and sealed with nitrogen, then sonicated in a cooled bath sonicator. Sonication was continued (for several seconds to several minutes depending on lipid quantity and nature) until the suspension became clear (suspension A) and there were no liposomes apparently visible under a phase contrast microscope with a 1000× magnification.

Step 2: Preparation of PFA-Loaded, Hydrogel-Isolated Cochleates

The liposome suspension obtained in Step 1 was mixed with 40% w/w dextran-500,000 in a suspension of 2/1 v/v Dextran/liposome. This mixture was injected via a syringe into 15% w/w PEG-8,000 (PEG 8000/(suspension A)) under magnetic stirring to result in suspension B. The rate of the stirring was 800–1,000 rpm. A CaCl$_2$ solution (100 mM) was added to the suspension to reach the final concentration of 1 mM.

Stirring was continued for one hour, and then a washing buffer containing 1 mM CaCl$_2$ and 150 mM NaCl was added to suspension B at the volumetric ratio of 1:1. The suspension was vortexed and centrifuged at 3000 rpm, 2–4° C. for 30 min. After the supernatant was removed, additional washing buffer was added at the volumetric ratio of 0.5:1, followed by centrifugation under the same conditions (see FIG. 1). The resulting pellet was reconstituted with the same buffer to the desired concentration.

Example 11

Preparation of Vanillin-Loaded Hydrogel-Isolated Cochleates Precipitated with Calcium Step 1: Preparation of Small Unilamellar Vitamin A-Loaded Vesicles from Dioleoylphosphatidylserine A mixture of dioleoylphosphatidylserine (DOPS) in chloroform (10 mg/ml) and Vanillin in methanol (0.5 mg/ml) at a molar ratio of lipid/vanillin of 10:1 was placed in a round-bottom flask and dried to a film using a Buchi rotavapor at RT. The rotavapor was sterilized by flashing nitrogen gas through a 0.2 µm filter. The following steps were carried out in a sterile hood. The dried lipid film was hydrated with de-ionized water at the concentration of 10 mg lipid/ml. The hydrated suspension was purged and sealed with nitrogen, then sonicated in a cooled bath sonicator. Sonication was continued (for several seconds to several minutes depending on lipid quantity and nature) until the suspension became clear (suspension A) and there were no liposomes apparently visible under a phase contrast microscope with a 1000× magnification.

Step 2: Preparation of Vanillin-Loaded, Hydrogel-Isolated Cochleates

The liposome suspension obtained in Step 1 was mixed with 40% w/w dextran-500,000 in a suspension of 2/1 v/v Dextran/liposome. This mixture was injected via a syringe into 15% w/w PEG-8,000 in a ratio of suspension A/PEG of ½ V/V (PEG 8000/(suspension A)) under magnetic stirring to result in suspension B. The rate of the stirring was 800–1,000 rpm. A CaCl$_2$ solution (100 mM) was added to the suspension to reach the final concentration of 1 mM.

Stirring was continued for one hour, and then a washing buffer containing 1 mM CaCl$_2$ and 150 mM NaCl was added to suspension B at the volumetric ratio of 1:1. The suspension was vortexed and centrifuged at 3000 rpm, 2–4° C. for 30 min. After the supernatant was removed, additional washing buffer was added at the volumetric ratio of 0.5:1, followed by centrifugation under the same conditions (see FIG. 1). The resulting pellet was reconstituted with the same buffer to the desired concentration. The amount of vanillin encapsulated in the cochleates was determined by UV absorption at 239 nm.

Example 12

Preparation of Cinnamon Oil (CinO)-Loaded Hydrogel-Isolated Cochleates Precipitated with Calcium Step 1: Preparation of Small Unilamellar CinO-Loaded Vesicles from Dioleoylphosphatidylserine A mixture of dioleoylphosphatidyl serine (DOPS) in chloroform (10 mg/ml) and CinO in methanol (0.5 mg/ml) at a molar ratio of 10:1 was placed in a round-bottom flask and dried to a film using a Buchi rotavapor at 40° C. The rotavapor was sterilized by flashing nitrogen gas through a 0.2 µm filter. The following steps were carried out in a sterile hood. The dried lipid film was hydrated with de-ionized water at the concentration of 10 mg lipid/ml. The hydrated suspension was purged and sealed with nitrogen, then sonicated in a cooled bath sonicator. Sonication was continued (for several seconds to several minutes depending on lipid quantity and nature) until the suspension became clear (suspension A) and there were no liposomes apparently visible under a phase contrast microscope with a 1000× magnification.

Step 2: Preparation of CinO-Loaded. Hydrogel-Isolated Cochleates

The liposome suspension obtained in Step 1 was mixed with 40% w/w dextran-500,000 in a suspension of 2/1 v/v Dextran/liposome. This mixture was injected via a syringe into 15% w/w PEG-8,000 (PEG 8000/(suspension A)) under magnetic stirring to result in suspension B. The rate of the stirring was 800–1,000 rpm. A CaCl$_2$ solution (100 mM) was added to the suspension to reach the final concentration of 1 mM.

Stirring was continued for one hour, and then a washing buffer containing 1 mM CaCl$_2$ and 150 mM NaCl was added to suspension B at the volumetric ratio of 1:1. The suspension was vortexed and centrifuged at 3000 rpm, 2–4° C. for 30 min. After the supernatant was removed, additional washing buffer was added at the volumetric ratio of 0.5:1, followed by centrifugation under the same conditions (see FIG. 1). The resulting pellet was reconstituted with the same buffer to the desired concentration.

Example 13

Preparation of DNA-Loaded Hydrogel-Isolated Cochleates Precipitated with Calcium Step 1: Preparation of Small Unilamellar DNA-Loaded Vesicles from Dioleoylphosphatidylserine A solution of dioleoylphosphatidylserine in chloroform (10 mg/ml) was placed in a round-bottom flask and dried to a film using a Buchi rotavapor at RT. The rotavapor was sterilized by flashing nitrogen gas through a 0.2 $\mu$m filter. The following steps were carried out in a sterile hood. The dried lipid film was hydrated with a solution of pCMV-beta-gal-DNA in TE buffer (at 1 mg/ml) to reach a concentration of DOPS:DNA of 10:1 and a concentration of 10 mg lipid/ml. The hydrated suspension was purged and sealed with nitrogen, then vortexed for several minutes.

Step 2: Preparation of DNA-Loaded, Hydrogel-Isolated Cochleates

The DNA/liposome mixture was mixed with 40% w/w dextran-500,000 in a suspension of 2/1 v/v Dextran/liposome. This mixture was injected via a syringe into 15% w/w PEG-8,000 (PEG 8000/(suspension A)) under magnetic stirring to result in suspension B. The rate of the stirring was 800–1,000 rpm. A $CaCl_2$ solution (100 mM) was added to the suspension to reach the final concentration of 1 mM.

Stirring was continued for one hour, and then a washing buffer containing 1 mM $CaCl_2$ and 150 mM NaCl was added to suspension B at the volumetric ratio of 10:1. The suspension was vortexed and centrifuged at 3000 rpm, 2–4 C, for 30 min. After the supernatant was removed, additional washing buffer was added at the volumetric ratio of 5:1, followed by centrifugation under the same conditions (see FIG. 1). The resulting pellet was reconstituted with the same buffer to the desired concentration.

Example 14

Preparation of Empty Hydrogel-Isolated Cochleates Precipitated with Zinc

Step 1: Preparation of Small Unilamellar Vesicles from Dioleoylphosphatidylserine A solution of dioleoylphosphatidylserine (DOPS) in chloroform (10 mg/ml) was placed in a round-bottom flask and dried to a film using a Buchi rotavapor at 35° C. The rotavapor was sterilized by flashing nitrogen gas through a 0.2 $\mu$m filter. The following steps were carried out in a sterile hood. The dried lipid film was hydrated with de-ionized water at the concentration of 10 mg lipid/ml. The hydrated suspension was purged and sealed with nitrogen, then sonicated in a cooled bath sonicator. Sonication was continued (for several seconds to several minutes depending on lipid quantity and nature) until the suspension became clear (suspension A) and there were no liposomes apparently visible under a phase contrast microscope with a 1000× magnification.

Step 2: Preparation of Hydrogel-Isolated Cochleates

The liposome suspension obtained in step 1 was mixed with 40% w/w dextran-500,000 in a suspension of 2/1 v/v Dextran/liposome. This mixture was injected via a syringe into 15% w/w PEG-8,000 (PEG 8000/(suspension A)) under magnetic stirring to result in suspension B. The rate of the stirring was 800–1,000 rpm. A $ZnCl_2$ solution (100 mM) was added to the suspension to reach the final concentration of 1 mM.

Stirring was continued for one hour, and then a washing buffer containing 1 mM $ZnCl_2$ and 150 mM NaCl was added to suspension B at the volumetric ratio of 1:1 . The suspension was vortexed and centrifuged at 3000 rpm, 2–4° C. for 30 min. After the supernatant was removed, additional washing buffer was added at the volumetric ratio of 0.5:1, followed by centrifugation under the same conditions (see FIG. 1). The resulting pellet was reconstituted with the same buffer to the desired concentration. Laser light scattering (weight analysis, Coulter N4 Plus) confirmed the formation of small cochleates.

Example 15

Preparation of Amphotericin B-Loaded Hydrogel-Isolated Cochleates Precipitated with Zinc Step 1: Preparation of Small Unilamellar AmB-Loaded Vesicles from Dioleoylphosphatidylserine A mixture of dioleoyl phosphatidylserine (DOPS) in chloroform (10 mg/ml) and AmB in methanol (0.5 mg/ml) at a molar ratio of 10:1 was placed in a round-bottom flask and dried to a film using a Buchi rotavapor at 40° C. The rotavapor was sterilized by flashing nitrogen gas through a 0.2 $\mu$m filter. The following steps were carried out in a sterile hood. The dried lipid film was hydrated with de-ionized water at the concentration of 10 mg lipid/ml. The hydrated suspension was purged and sealed with nitrogen, then sonicated in a cooled bath sonicator. Sonication was continued (for several seconds to several minutes depending on lipid quantity and nature) until the suspension became clear yellow (suspension A) and there were no liposomes apparently visible under a phase contrast microscope with a 1000× magnification.

Step 2: Preparation of AmB-Loaded. Hydrogel-Isolated Cochleates

The liposome suspension obtained in Step 1 was mixed with 40% w/w dextran-500,000 in a suspension of 2/1 v/v Dextran/liposome. This mixture was injected via a syringe into 15% w/w PEG-8,000 (PEG 8000/(suspension A)) under magnetic stirring to result in suspension B. The rate of the stirring was 800–1,000 rpm. A $ZnCl_2$ solution (100 mM) was added to the suspension to reach the final concentration of 1 mM.

Stirring was continued for one hour, and then a washing buffer containing 1 mM $ZnCl_2$ and 150 mM NaCl was added to the suspension B at the volumetric ratio of 1:1 . The suspension was vortexed and centrifuged at 3000 rpm, 2–4° C. for 30 min. After the supernatant was removed, additional washing buffer was added at the volumetric ratio of 0.5:1, followed by centrifugation under the same conditions (see FIG. 1). The resultant pellet was reconstituted with the same buffer to the desired concentration. Laser light scattering (weight analysis, Coulter N4 Plus) confirmed the formation of small AmB-Zn-cochleates.

Example 16

Microscopic Observation of Hydrogel-Isolated Cochleates Optical microscopic study was performed stepwise alone with the preparation procedure in order to gain some mechanistic details of the formation of the hydrogel-isolated cochleates.

The microscopic images seen in FIGS. 3A, 3B and 4A–4F show the morphological changes at each preparation step of AmB loaded hydrogel-isolated cochleates precipitated with Ca$_{2+}$ ions. When the AmB/liposome-dextran mixture was dispersed into PEG solution, phase separation resulted as shown by FIG. 3A. Partition of the liposomes favored the dispersed dextran phase as indicated by a yellow color of AmB. This partitioning ensures that liposomes are isolated in each dextran particle. Addition of Calcium ions into the continued phase (PEG) resulted in formation of precipitates in the dispersed phase. As the final product, small needle-shape cochleates were formed and observed under the microscope, these cochleates opened into unilamellar vesicles upon addition of EDTA and chelation of the calcium (FIGS. 4A and 4B). The needle-shaped morphology was confirmed by scanning electron microscopy after freeze-fracture (FIG. 5). Similar microscopic images were obtained for empty and AmB-Zn-precipitated hydrogel-isolated cochleates (FIGS. 4C and 4D) and empty Zn-precipitated hydrogel-isolated cochleate (FIGS. 4E and 4F).

Example 17

Antifungal Activity of Hydrogel-Isolated Cochleates Loaded with Amphotericin B. In Vitro Growth Inhibition of *Candida albicans*

An in vitro yeast susceptibility assay was performed comparing the inhibitory and lethal effects of AmB-cochleates, AmBisomes (liposomal formulation of AmB) and AmB/DMSO. Five colonies of freshly growing *Candida albicans* were selected from a YPD agar plate (from a 48 hour g culture) and added to 2 ml of 2× YPD broth, pH 5.7. The OD$_{590}$ of this stock culture was measured and the yeast density was adjusted to OD$_{590}$=0.1 and 0.1 ml of this suspension added to each well of a 96 well plate. AmB/cochleates, AmB/DMSO and AmBisomes were added to 96 well plates to a final concentration of 0.078, 0.156, 0.3125, 0.625, 1.25 and 2.5 µg/ml of AmB. The 96 well plates were incubated at 37° C. with gentle shaking and cell density was measured on a 96 well plate reader (Molecular Devices Spectramax 340) at 0, 2, 4, 6, 24 and 30 hours. FIG. 6 shows that AmB-cochleates have a greater growth inhibitory effect than AmBisomes (liposomal formulation of AmB).

Fungicidal Effect of Hydrogel-Isolated Cochleates Loaded with Amphotericin B

Aliquots of yeast cells (50 µl) were removed from the 96 well plates and serially diluted (up to 1:10000 for plating onto agar plates) and counted using a hemocytometer. Fifty µl of the diluted yeast cells were plated onto YPD agar plates and incubated for 24 hours at 37° C. Yeast colonies were counted using a BioRad Fluor-S Multi-Imager equipped with Quanitity One™ software.

Yeast cells treated with AmBisome, AmB/DMSO and AmB/cochleates (0.625 µg AmB/ml) were examined for the ratio of colony forming units to total cell number after 30 hours of incubation. The results show that the AmB/cochleates had the greatest lethal effect on the yeast cells compared to the other antifungal agents tested. There was nearly 0% yeast viability after treatment with the AmB-cochleates and 12% yeast viability after treatment with AmB/DMSO. The AmBisome was not as effective, resulting in 52% yeast viability (FIG. 7).

Macrophage Protection with AmB Cochleates

Particle scavenging cells, such as macrophage, are the first line of defense against many microbial infections. However, many microbes, which induce severe human clinical infections, have been shown to infect macrophage and avoid destruction.

It is possible that in vivo, macrophage play an important role in the uptake of cochleates, via an endocytotic mechanism. Since macrophage also play an important role in the host defense and clearance of fungi and parasites, it is important to study the interaction between macrophage and cochleates.

The following examples indicate that the cochleates are taken up by macrophage. Large doses of AmB delivered to the macrophage were found to be non-toxic and remained within the macrophage in a biologically active form. AmB cochleates provided protection for the macrophage against infection by *Candida albicans* when administered prior to or after fungal infection.

Prophylactic dose regime: J774A.1 macrophage (M) were subcultured into a 96-well plate at a concentration of 1×10$^5$ cells/ml in DMEM+10% FBS. One-hundred µl AmB cochleates (AmBc 0.2, 0.6, 1.25, and 2.5 µg AmB/ml), Fungizone, or empty cochleates (EC at 2, 6, 12.5, and 25 µg lipid/ml) were added at the specified concentration. Plates were incubated overnight at 37° C. and 5% CO$_2$. 24 hours later, the medium was replaced. This step was performed twice. *Candida albicans* (CA) was added to the plate at a concentration of 2.5×10$^3$ cells/ml, a ratio of 1:200 with respect to the macrophage. Plates were incubated overnight under the conditions stated above.

Following the 24 hr incubation, the plates were removed and observed. Medium was pipetted vigorously to remove and disrupt the cells, 25 µl of this suspension was placed onto Sabouraud Dextrose Agar plates, and then placed in a dry incubator overnight at 37° C. *Candida albicans* CFU's were counted the following day. The data in FIG. 8A suggest that AmB cochleate loaded macrophage are very effective at killing the fungal cells.

Post-infection dose regime: J774A1. macrophage (M) were subcultured into a 96-well plate and then incubated overnight. Following incubation, the macrophage were infected with CA at a ratio of 200:1, then subsequently AmBc, Fungizone or EC was added at the specified concentrations. Twenty-four hours later, the cell cultures were observed and CFU's determined as described above.

When M were challenged with CA and subsequently dosed with AmB cochleates, the CFU count was again nearly zero. These results indicate that macrophage engulf and concentrate AmB cochleate, as macrophage were protected against *Candida albicans* challenge after AmB cochleate had been washed off (FIG. 8B).

In contrast, Fungizone, (AmB in deoxycholate), the most popular clinical form of AmB was extremely toxic and lethal to the macrophage in vitro. Within 5 hours of administration, there was a large amount of cellular debris found in the petri dish, with no signs of viable macrophage.

Microscopic observation reveals the AmB cochleates are not toxic to the macrophage even at the highest doses studied. The AmB cochleates are accumulated at high levels resulting in large distended vacuoles. After washing of the macrophage and incubating again for 24 hours, most of the vacuoles had returned to the normal shape and size, yet a few were noticeably enlarged. A few macrophage were even noticed to be "moving" with the enlarged vacuoles. AmB cochleates are concentrated within the vacuoles and it is probable that AmB is released gradually over time.

Example 18

Evaluation of Tissue Penetration of AmB after IV Administration of Amphotericin B Hydrogel-Isolated Cochleates Tissue penetration of amphotericin B has been evaluated after IV administration. Groups (n=5) of C57BL/6 mice (20–23 g) were given IV (0.625 mg/kg) AmB cochleates (0.05 ml/20 g) with a ½ cc U 100 insulin syringe with a 18 g ½ needle size. At predetermined sacrifice times (2, 5, 10, 20 and 40 min, 1, 2, 3, 4, 6, 8, 12, 24, 36 and 48 hrs), animals were given anesthesia, their blood was collected via cardiac puncture, and then, the animals were euthanized and dissected. Tissues of interest were removed (brain, lung, liver, spleen, kidneys, heart, fat, stomach, stomach contents, intestine and intestinal contents) and weighed. For analysis of AmB, samples were mixed with extraction solvent (10% methanol, 35% water, 55% ethanol), homogenized, sonicated and centrifuged. A 90 µl aliquot of supernatant was transferred into a micro vial, injected into the HPLC system in a Nova-Pak C-18 column (3.9×150 mm, 4 µm particle size), and kept at 40° C. Amphotericin B was eluted at a flow rate of 0.5 ml/min with 29% methanol, 30% acetonitrile and 41% 2.5 mM EDTA and then detected at 408 nm. The concentration of AmB was calculated with the help of an external standard curve.

In FIG. 9 the tissue exposure after a single IV dose of AmB cochleates is shown. Large penetration of key tissues like liver, spleen and kidney can be observed.

Example 19

Oral Delivery of AmB Mediated by Hydrogel-Isolated Cochleates Loaded with AmB

Single Dose Regime

Oral availability of the hydrogel-isolated cochleates loaded with AmB has been examined by intragastric administration of the formulation of example 4 to overnight fasting, C57BL16 mice (20–23 g). 1/10 ml of the formulation at the dose of 10 mg/kg was administrated to 9 mice. Three mice from each group were sacrificed at 1, 6 and 24 hrs post administration followed by analysis of AmB level in organs and tissues.

Tissue and blood samples were processed as follows: tissues were diluted 1/20 or 1/10 by addition of extraction solvent ($H_2O$ 35%, methanol 10%, ethanol 55% w/w/w nv/v/v) and homogenized with an Ultra-Turrex® device. A 0.5 ml aliquot was taken, sonicated for 1 min and centrifuged at 7260 rpm for 12 min at 4° C. Supernatant was transferred to an HPLC micro-vial and 30 µl was injected on a C-18, 3.9×150 mm, 4 µm particle sized analytical column with a flow rate of 0.5 ml, at 40° C. Concentration of AmB detected at 408 nm was calculated with the help of an external calibration curve.

FIG. 10 shows the time profile of AmB in the tissues over a period of time of 24 hrs. Although only three time points are plotted, accumulation in key tissues (liver, lungs, spleen and kidneys) can be seen.

Multiple Dose Regime

Two other groups of mice received a 10 mg/kg/day oral multiple dose regime for ten days and one group was sacrificed 24 hrs after the last dose and the other group 20 days after the last dose received. At the predetermined time points mice were anesthetized, sacrificed and dissected for tissue collection. Tissues were processed as in the single dose regime and the AmB level was determined by HPLC. Results from 24 hr after the $10^{th}$ dose are depicted in FIG. 11 and show that hydrogel-isolated cochleates allow the delivery of AmB from the gastrointestinal tract at therapeutic levels.

Example 20

Correlation Between Biodistribution in Healthy and Infected Mice and the Level of *Candida albicans* in Tissue after Oral Administration FIG. 12 shows the relationship between tissue levels of Amphotericin B (µg/g tissue on left scale) and efficacy as decrease of *Candida albicans* infection (CFU/g on the right scale) after oral administration of AmB-cochleates.

After oral administration of 10 mg/kg/day for 10 consecutive days to healthy mice, AmB presented high levels in kidneys followed by lungs, spleen, liver and brain, which shows much lower levels than the other tissues. It has been shown that disease state affects pharmacokinetics of drugs at different levels. This phenomenon can be seen clearly in the graph: AmB in tissue reaches lower levels in *Candida albicans* infected mice after oral administration of 10 mg/kg/day (same dose) for 15 days, 5 more doses than the healthy group. It also shows a change in the distribution pattern where the lungs are the target tissue with lowest levels.

Oral administration of an AmB cochleate formulation at 10 mg/kg/day for 15 days provided high efficacy. The decrease in CFU/g in kidney tissue is about 3.5 logs for the cochleate formulation. In lungs, AmB cochleate formulations completely eradicate *Candida albicans* and clear the lungs of fungal infection. It is clear that the cochleate delivery system provides a high level of AmB in infected animals, this correlates with the higher efficiency seen in the cochleate formulation, indicating that AmB-cochleates are a suitable vehicle for oral treatment of systemic Candidiasis.

In addition, orally administered AmB-cochleates were non-toxic even at the highest dose of 50 mg/kg (no lesions were found in kidneys, GI tract and other organs of mice given 10, 20 and 50 mg/kg of AmB-cochleates). This high dose (50 mg/kg) is equivalent to 100 times the lowest dose (0.5 mg/kg) that showed 100% of survival in the Candida infected mouse model.

What is claimed:

1. A method for producing a lipid-based cochleate comprising the steps of:
   a) providing an aqueous suspension containing a detergent-lipid mixture;
   b) mixing the detergent-lipid suspension with polymer A;
   c) adding the detergent-lipid/polymer A suspension into a solution comprising polymer B, wherein polymer A and polymer B are immiscible, thereby creating a two-phase polymer system;
   d) adding a solution of a cationic moiety to the two-phase polymer system; and
   e) washing the two-phase polymer system to remove the polymer.

2. The method for producing the lipid-based cochleate according to claim 1, wherein the resulting cochleate has a mean particle size of less than one micron.

3. The method for producing the lipid-based cochleate according to claim 1, wherein the detergent is octyl glucoside.

4. The method for producing the lipid-based cochleate according to claim 1, wherein the cochleate comprises a biologically relevant molecule.

5. The method according to claim 1, wherein the biologically relevant molecule is added in step (a).

6. The method according to claim 1, wherein the washing step comprises centrifuging the two-phase polymer system to separate the cochleate precipitate, removing the supernatant containing the polymer, resuspending the precipitate in a washing buffer, centrifuging the washed precipitate, and optionally repeating the resuspension and centrifugation steps one or more times.

7. The method according to claim 6, wherein the washing buffer contains dissolved cationic moiety.

8. The method according to claim 7, wherein the cationic moiety comprises di- or higher- valent ions.

9. The method according to claim 7, wherein the di- or higher-valent ions are metal ions.

10. The method according to claim 9, wherein the metal ions are a member selected from the group consisting of a calcium and a zinc.

11. The method according to claim 7, wherein the cationic moiety is present in the washing buffer at a concentration of at least 1 mM.

12. The method according to claim 1, wherein the biologically relevant molecule bears a charge.

13. The method according to claim 12, wherein the biologically relevant molecule bears a positive charge.

14. The method according to claim 12, wherein the biologically relevant molecule bears a negative charge.

15. The method according to claim 1, wherein the biologically relevant molecule is amphiphilic.

16. The method according to claim 1, wherein the biologically relevant molecule is hydrophobic.

17. The method according to claim 1, wherein the biologically relevant molecule is at least one member selected from the group consisting of a drug, a polynucleotide, a polypeptide, an antigen, a nutrient and a flavor substance.

18. The method of claim 17, wherein the drug is at least one member selected from the group consisting of an antiviral, an anesthetic, an anti-infectious, an antifungal, an anticancer, an immunosuppressant, a steroidal anti-inflammatory, a non-steroidal anti-inflammatory, a tranquilizer, and a vasodilatory agent.

19. The method of claim 18, wherein the drug is at least one member selected from the group consisting of Amphotericin B, acyclovir, adriamycin, carbamazepine, melphalan, nifedipine, indomethacin, naproxen, estrogens, testosterones, steroids, phenytoin, ergotamines, cannabinoids, rapamycin, propanidid, propofol, alphadione, echinomycine, miconazole nitrate, teniposide, taxol, taxotere, nystatin, rifampin, and vitamin A acid.

20. The method according to claim 17, wherein the polynucleotide is at least one member selected from the group consisting of a deoxyribonucletic acid (DNA) molecule, a ribonucleic acid (RNA) molecule, a ribozyme, an antisense molecule, and a plasmid.

21. The method according to claim 20, wherein the DNA is transcribed to yield a ribonucleic acid.

22. The method according to claim 21, wherein the ribonucleic acid is translated to yield a biologically active polypeptide.

23. The method according to claim 17, wherein the polypeptide is at least one member selected from the group consisting of cyclosporin, angiotensin I, II, or III, enkephalins and their analogs, ACTH, anti-inflammatory peptides I, II, or III, bradykinin, calcitonin, beta-endorphin, dinorphin, leucokinin, leutinizing hormone releasing hormone (LHRH), insulin, neurokinins, somatostatin, substance P, thyroid releasing hormone (TRH), and vasopressin.

24. The method according to claim 17, wherein the antigen is at least one member selected from the group consisting of a carbohydrate, envelope glycoproteins from viruses, an animal cell membrane protein, a plant cell membrane protein, a bacterial membrane protein and a parasitic membrane protein.

25. The method according to claim 17, wherein the nutrient is at least one member selected from the group consisting of vitamins, minerals, fatty acids, amino acids, and saccharides.

26. The method according to claim 17, wherein the vitamin is at least one member selected from the group consisting of vitamins A, D, E, and K.

27. The method according to claim 17, wherein the mineral is at least one member selected from the group consisting of calcium, magnesium, barium, iron and zinc.

28. The method according to claim 17, wherein the fatty acid is at least one member selected from the group consisting of polyunsaturated and saturated fatty acids.

29. The method according to claim 17, wherein the saccharide is at least one member selected from the group consisting of glucose and sucrose.

30. The method according to claim 17, wherein the flavor substance is at least one member selected from the group consisting of botanical essential oils and extracts.

31. The cochleate composition according to claim 30, wherein the essential oil is a cinnamon oil.

32. The method according to claim 30, wherein the extracts are from at least one member selected from the group consisting of an herb, a citrus, a spice and a seed.

33. Cochleates containing a biologically relevant molecule prepared according to any one of claims 1–32.

34. A pharmaceutical composition comprising an effective amount of the cochleate composition of claim 33, and a pharmaceutically acceptable carrier.

35. A method of treatment comprising administering to a human or animal host a pharmaceutically effective amount of the pharmaceutical composition according to claim 34.

36. The method of treatment according to claim 35, wherein the administration is by a mucosal or a systemic route.

37. The method of treatment according to claim 35, wherein the ministration is a mucosal route selected from the group consisting of oral, intranasal, intraocular, intraanal, intravaginal, and intrapulmonary.

38. The method of treatment according to claim 35, wherein the administration is by a systemic route selected from the group consisting of intravenous, intramuscular, subcutaneous, transdermal and intradermal.

* * * * *